United States Patent [19]

Bruinvels et al.

[11] 4,156,013
[45] May 22, 1979

[54] METHOD FOR TREATING PATIENTS SUFFERING FROM ANXIETY NEUROSIS AND ANXIETYLIKE NEUROSIS, AND ALCOHOLISM

[75] Inventors: Jacques Bruinvels, de Bilt; Lolke Pepplinkhuizen, Rotterdam, both of Netherlands

[73] Assignee: Erasmus Universiteit Rotterdam, Rotterdam, Netherlands

[21] Appl. No.: 914,087

[22] Filed: Jun. 9, 1978

[30] Foreign Application Priority Data

Jun. 10, 1977 [NL] Netherlands .......................... 7706429

[51] Int. Cl.$^2$ ............................................ A61K 31/195
[52] U.S. Cl. ..................................................... 424/319
[58] Field of Search ......................................... 424/319

[56] References Cited

PUBLICATIONS

Chem. Abst. 59-8646G (1963).

Primary Examiner—Stanley J. Friedman
Attorney, Agent, or Firm—Mason, Fenwick & Lawrence

[57] ABSTRACT

Patients suffering from anxiety neurosis and anxietylike neurosis often accompanied by alcoholism are treated by administration of medicine containing a β-(p-halogen phenyl)-γ-aminobutyric acid as active compound. As a result these patients were totally freed from the above mentioned complaints.

5 Claims, 1 Drawing Figure

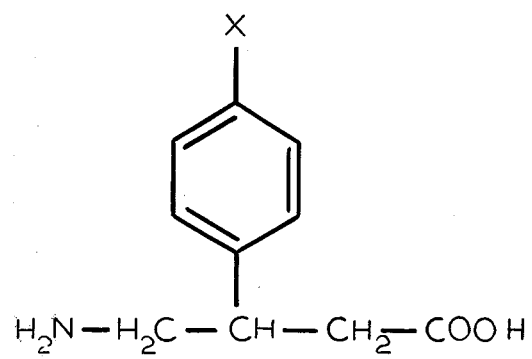

METHOD FOR TREATING PATIENTS SUFFERING FROM ANXIETY NEUROSIS AND ANXIETYLIKE NEUROSIS, AND ALCOHOLISM

The invention relates to a process for the preparation of a medicine having anti-anxiety neurosis and anti-anxietylike neurosis activity and to a medicine having such activity.

From clinical trials it appeared that patients having anxiety neurosis, as defined by Woodruff, R. A., Goodwin, D. W. and Guze, S. B. and Wheeler, E. O., White, P. D., Reed, E. W. and Cohen, M. E., did not show any amelioration upon administration of known anxiolytics.

The symptoms of anxiety neurosis, as defined by Woodruff and Wheeler, are in decreasing significancy: palpitation, tires easily, breathlessness, nervousness, chest pain, sighing, dizziness, faintness, apprehensiveness, headache, paresthesias, weakness, trembling, breath unsatisfactory, insomnia, unhappiness, shakiness, fatigued all the time, sweating, fear of death, smothering, syncope, urinary frequency, vomiting and diarrhea and anorexia.

Such patients, who very often suffer from serious sleep disorders, do not react at all or hardly react on the administration of well known anxiolytics or sleep inducing medicines, such as benzodiazepines or barbiturates, among others valium, seresta, temesta, vesparax etc. Also an intensive psycho-therapy did not provide the desired results.

If one realizes that 2-4% of the population suffers from such anxiety neurosis, it should be clear that there exists a pressing need in providing a medicine having anti-anxiety neurosis and anti-anxietylike neurosis activity.

The object of the invention is to meet such a need.

In this connection the invention relates to a process for the preparation of a medicine possessing anxiety neurosis, characterized in that a compound having the formula of the formula sheet, wherein X is a halogen atom, such as Fl, Cl or Br, is put in an administration form which is suited for medical purposes.

As active compound a $\beta$-(p-halogen phenyl)-$\gamma$-amino/butyric acid is used. In the event that in the compound having the formula of the formula sheet X is Cl, this compound is a known substance, to wit $\beta$-(p-chloro phenyl)-$\gamma$-aminobutyric acid having the generical name of baclofen. It is well known that this compound possesses muscle relaxing activity and is used as such.

Surprisingly it has been found that upon administration of baclofen to a certain group of patients suffering from the above anxiety neurosis drastical amelioration of their situation occurred, which means that the patients were completely or practically completely freed from the symptoms belonging to the anxiety neurosis. They could again normally functionate in society.

This amelioration occurred with all treated patients suffering from anxiety neurosis, of which the anxiety neurosis seemed to be of family nature. These patients, having a positive reaction on the administration of baclofen, had a hypoplastical-leptosomical-build.

Patients, who did not fulfil the above mentioned conditions, appeared not to react on the administration of baclofen.

In order to achieve the desired results it appeared necessary to administrate the active compound first in a dosage of 15-60 mg per day, dependent on the nature and the age of the patient and the seriousness of the neurosis. After certain time a supporting dosage of 5-15 mg per day was sufficient. The preferred dosage is determined individually.

Preferably the active compounds are administrated as suppositoria or coated tablets, since in oral administration in the form of uncoated tablets these patients often suffer from stomach-complaints, which may be such that the administration should be discontinued.

It is known, that several patients, suffering from anxiety neurosis of the above mentioned type have recoursed to an excessive use of alcohol, often followed by chronical alcohol misuse. Apparently the alcohol was the only drug that helped up to now.

Surprisingly it has been found too that patients of the above mentioned special group, who furthermore have a tendency to alcohol misuse, were not only freed from the anxiety neurosis symptoms, but also from their craving for alcohol.

We claim:

1. A method for treating patients suffering from anxiety neurosis, which comprises administering to said patients a compound having the formula

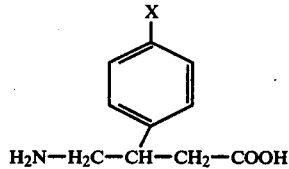

wherein X is a halogen atom such as Fl, Cl or Br, in a dose sufficient to relieve the symptoms of said neurosis.

2. The method of claim 1 including said dose being in an amount of about 5-60 mg per day per patient.

3. The method of claim 1 including, said dose being initially 15-60 mg per day per patient and thereafter 5-15 mg per day per patient.

4. The method of claim 2 including, said dose being in the form of suppositoria or coated tablets.

5. The method of claim 1 where the anxiety neurosis is accompanied by alcoholism.